(12) United States Patent
Holbeche et al.

(10) Patent No.: US 9,072,157 B2
(45) Date of Patent: Jun. 30, 2015

(54) DEVICE FOR PROVIDING A FLOW OF ACTIVE GAS

(75) Inventors: Thomas Bickford Holbeche, Church Crookham (GB); Richard Thomas Reich, Farnham (GB); Peter Dobson, Rowledge (GB); Cormac John Devery, Felbridge (GB); Andrew Richard Thomas Tatarek, Aldershot (GB)

(73) Assignee: Linde Aktiengesellschaft, Munich (DE)

( * ) Notice: Subject to any disclaimer, the term of this patent is extended or adjusted under 35 U.S.C. 154(b) by 597 days.

(21) Appl. No.: 13/083,699

(22) Filed: Apr. 11, 2011

(65) Prior Publication Data

US 2011/0306006 A1 Dec. 15, 2011

(51) Int. Cl.
*B01J 19/08* (2006.01)
*H05H 1/24* (2006.01)
*A61B 18/04* (2006.01)
*A61C 17/02* (2006.01)

(52) U.S. Cl.
CPC ............... *H05H 1/24* (2013.01); *A61B 18/042* (2013.01); *A61C 17/02* (2013.01)

(58) Field of Classification Search
CPC ......... H05H 1/24; A61B 18/042; A61C 17/02
USPC .................................................... 422/186.04
See application file for complete search history.

(56) References Cited

U.S. PATENT DOCUMENTS

| | | | |
|---|---|---|---|
| 6,455,014 B1 * | 9/2002 | Hammerstrom et al. | 422/186.04 |
| 7,633,231 B2 | 12/2009 | Watson | |
| 2009/0004620 A1 | 1/2009 | Liu et al. | |
| 2010/0130911 A1 | 5/2010 | Morfill et al. | |

FOREIGN PATENT DOCUMENTS

| | | | |
|---|---|---|---|
| CN | 101229079 A | | 7/2008 |
| CN | 101259036 A | | 9/2008 |
| WO | WO 03/041112 A2 | | 5/2003 |
| WO | WO 2007/067924 | * | 6/2007 |
| WO | WO 2009/128579 A1 | | 10/2009 |
| WO | WO 2010008062 A1 | | 1/2010 |
| WO | WO 2010/103263 A1 | | 9/2010 |

OTHER PUBLICATIONS

Hong et al., "Microplasma jet at atmospheric pressure", Applied Physics letters 89, 221504, (2006).*
European Search Report, Sep. 29, 2010.
European Search Report, Aug. 16, 2010.

* cited by examiner

*Primary Examiner* — Kishor Mayekar
(74) *Attorney, Agent, or Firm* — David A. Hey

(57) ABSTRACT

A device 10, typically hand-held, provides a flow of partially ionized gaseous plasma for treatment of a treatment region. The device comprises an applicator head 52 housing a miniature plasma cell 16 in which gas flowing through the cell from a gas source 22 can be energized to form a non-thermal gaseous plasma, and a plurality of electrodes 26, 28 for receiving electrical energy from a source of electrical energy for energizing gas in a plasma forming region 18 in the cell to form said plasma. The applicator head 52 is detachable from the device and may be of a size and configuration to enable it to be inserted into the oral cavity of a human or animal.

11 Claims, 2 Drawing Sheets

DEVICE FOR PROVIDING A FLOW OF ACTIVE GAS

BACKGROUND OF THE INVENTION

The present invention relates to a device for providing a flow of active gas. In particular the invention is directed towards a device used which generates non-thermal plasma for treating an oral region of a human or animal body.

Systems for the generation of non thermal gas plasmas are known and have utility in a number of fields such as industrial, dental, medical, cosmetic and veterinary fields for the treatment of the human or animal body. Non-thermal gas plasma generation can be employed to promote coagulation of blood, cleaning, sterilisation and removal of contaminants from a surface, disinfection, reconnection of tissue and treatment of tissue disorders without causing significant thermal tissue damage.

Hereto, the application of non-thermal plasmas has been confined to controlled environments, such as in industry or clinics, since there is risk associated with the generation of plasmas with high electrical potentials, which if transmitted to a patient can cause injury or fatalities. The use of a plasma in a consumer product has therefore been limited, where controlled use of plasma generation cannot be assured.

Typically, in plasma generation energy is applied to a gas or gas mixture for ionising the molecules or atoms of the gas producing an ionic species, or plasma. Energy is supplied to the gas either by inductive or capacitive coupling. Electrodes are provided for supplying energy to gas in a plasma cell and in order to protect a patient from the high electrical potential of the electrodes, the electrodes have been insulated with a dielectric material. However, such an arrangement has been found to have draw-backs, since the use of a dielectric reduces the effective potential of the electrode and therefore requires a source of higher potential to drive the electrodes. A higher potential source is either more expensive or may be drained more quickly, particularly in a consumer device in which the source is one or more batteries. Further, electrodes having dielectric insulation are driven by alternating current which can pass through the electrode arrangement potentially causing injury to a user.

In the context of this application, the term cold, or non-thermal plasma means that the plasma has a temperature of less than about 40° C. which is a temperature tolerable to a patient without causing injury or discomfort. Such plasmas have only a small proportion of the gas molecules in an ionised state.

In typical generators of non-thermal plasma, the plasma generation cell is remote from an applicator which in use is positioned adjacent to a region to be treated ('treatment region'). There are several disadvantages to such arrangements. In particular, difficulties may arise in obtaining an adequate concentration of active species at the treatment region as a result of decaying numbers of active species as the gas flows from the remote plasma cell to the treatment region and because the performance of the plasma cell may deteriorate with time.

SUMMARY OF THE INVENTION

According to the present invention there is provided a device for providing a flow of partially ionised gaseous plasma for treatment of a treatment region, the device comprising a miniature plasma cell defining a volume in which gas passing through a cell inlet from a gas source can be energised to form a non-thermal gaseous plasma and discharged through a cell outlet, and a plurality of electrodes for receiving electrical power for energising gas in the cell to form said non-thermal plasma gaseous, wherein the device comprises an applicator head which is configured for location adjacent a treatment region, the applicator head is detachable from the device and the plasma cell is located in the applicator head.

The device is preferably hand-held.

The invention also provides a hand-held device for providing a flow of partially ionised plasma for treatment of a treatment region, the device comprising an applicator head and a miniaturised plasma cell defining a volume in which gas passing through a cell inlet from a gas source can be energised to form a non-thermal gaseous plasma and discharged through a cell outlet for treatment of a treatment region by said generated plasma, wherein the plasma cell has a location in the applicator head.

Plasma generation may occur for example by glow discharge and arcing or streaming. In the latter, current flows through the plasma cell from one electrode to another and plasma is generated in the vicinity of the arc or stream. Plasma is not generated in the volume of the cell away from the arc even though that volume may be located between the electrodes. Arcing typically takes place because of the imperfect nature of the electrode surfaces such that current flow may be favoured at only a very small portion of the electrodes. Once current begins to flow there is a cascade effect which increases plasma generation at this small portion but deprives the flow at other areas of the electrodes. In glow discharge, arcing does not occur and plasma is generated generally homogeneously between the electrodes, leading to an increased production of plasma for gas flowing through the plasma cell. Given that the size of a gas source in a hand-held consumer device is limited, gas must be used efficiently to prolong the life of the device between refills. It is also generally important to reduce power consumption, again to prolong useful life between battery replacement or recharge. It is desirable therefore to keep the voltage required to generate plasma in the cell to a minimum.

In a first preferred aspect of the invention, the electrode configuration maintains glow discharge and generally avoids arcing between the electrodes. In this way, homogeneity of plasma generation can be increased which conserves both power and gas. The electrodes may comprise electrical conductors or barrier to barrier capacitive coupled electrodes.

One way in which this can be achieved is by the arrangement of at least one of said electrodes so that it comprises an array of electrode portions, each of which in use energises gas in the plasma forming region, wherein the electrode portions are distributed over said plasma forming region for increasing homogeneity of plasma generation of gas flowing through the plasma cell. This arrangement reduces the occurrence of arcing since there are many electrode portions and therefore arcing at any one portion of the electrode is reduced.

In a preferred array, said electrode portions comprise respective electrical conductors which in use transmit electrical charge to gas flowing through the cell and each electrode portion comprises an electrical resistor connected between the electrical conductor and the source of electrical energy so that when any one first electrode portion generates plasma in the plasma forming region, the electrical potential is reduced by the flow of current through the resistor of said first electrode portion so that the potential at the other of the electrode portions is higher than at said first electrode portion. Accordingly, electrical energy is diverted from an electrode portion which has already generated to plasma to those electrodes which have yet to generate plasma. There are two benefits of this arrangement. First, when electrode portion has ignited plasma it requires less energy for sustaining the plasma. Second, it reduces the concentration of current at any one electrode which may lead to arcing and reduced efficiency of gas usage.

An insulated electrical plate may located in the cell for conducting electrically energy to each of the electrode portions.

In order to spread the passage of current at first exposed ends of the electrode portions, preferably the ends comprise respective curved electrically conductive elements, such as metal balls, from which electrical energy is discharged for forming said plasma.

From a safety aspect, it is preferred that the electrode which is positioned in use closest to the treatment region is at the same potential as a user, particularly if the treatment region is an oral cavity. Accordingly, the electrodes comprise a first electrode which receives an electrical potential for transmitting charge to gas flowing through the cell and a second electrode which in use is maintained at a potential generally equal to that of a user, and the second electrode is located downstream of the first electrode relative to the flow of gas.

In alternative arrangement for making efficient use of gas flow through the plasma cell, the plasma forming region is generated in use by arcing between the electrodes and the cell and the location of the electrodes is configured so that a substantial portion of gas flowing through the cell passes through said plasma forming region for increasing homogeneity of plasma generation. Although in this arrangement arcing occurs, the location of the arcing is controlled so that it is in the flow path of the gas and substantially all of the gas flows through the energised region where arcing occurs. Accordingly, homogeneity of plasma generation can be achieved.

In either glow discharge or arcing arrangements, at least one electrode is preferably located at the outlet of the cell for drawing plasma through the outlet and encouraging its passage to the treatment region. In the arcing arrangement, the electrodes may be arranged such that arcing occurs substantially throughout the area of the outlet so that any gas passing through the cell must interact with the discharge between the electrodes when it exits the cell through the outlet. In general, glow discharge is preferred.

A predetermined flow of plasma is generally required for beneficial treatment of a treatment region. A miniaturised plasma cell is advantageous in that it is able to supply this beneficial flow but also conserve gas and power to the extent possible. In a miniaturised plasma cell, the spacing between the electrodes is reduced, preferably to no more than 10 mm. In some arrangements, the electrode spacing can be considerably less than 10 mm and may be as little as 0.1 mm. The reduced spacing reduces power usage because all of the gas passing through the plasma forming region between the electrodes is exposed to substantial amounts of energy. In this regard, plasma generation may occur more readily in the volume of the plasma generating region proximate the electrode surfaces and therefore reduced spacing increases the efficiency of plasma production per unit of energy supplied. The plasma cell may have a free gas space of between 1 and 5 ml or less.

In another possible arrangement, a miniature array of miniature plasma cells is provided which each receive in use gas from a source of gas and a plurality of said electrodes for energising gas in the plasma cells to generate a plasma. This arrangement reduces the propensity of current hogging at any one electrode and therefore improves homogeneity of plasma production.

The applicator head is preferably configured for location in an oral cavity of a human or animal for treating the teeth or gingival of the human or animal. In order to achieve location in a mouth and particularly for manipulation by a user in the mouth for treating teeth, there is a workable upper limit to the size of the applicator and hence the size of the plasma cell. In one arrangement, the applicator head may be similar in size to that of a typical tooth brush head. If desired, the applicator head may be a toothbrush head provided with the bristles as well as an outlet part or parts for active gas flowing from the plasma cell.

A housing is typically provided for housing a gas source and source of electrical power, the housing having a connection portion for connecting to a complementary connecting portion of the applicator head so that when connected gas can be supplied to the cell and the electrodes supplied with electrical power. The applicator head and plasma cell may be disposable after a recommended period of use. In this regard, the present invention also covers an applicator head, which may be supplied separately from the device, comprising the plasma cell and electrode arrangement.

If desired, the device according to the invention may instead of being hand-held may be formed as an attachment to an articulated arm of a kind that is used to hold a dentist's drill.

The present invention further provides a miniaturised plasma cell and electrode arrangement for a device as described.

BRIEF DESCRIPTION OF THE DRAWINGS

In order that the invention may be more clearly understood reference will now be made to the accompanying drawings, given by way of example only, in which.

DETAILED DESCRIPTION OF PREFERRED EMBODIMENTS

Figure 1:
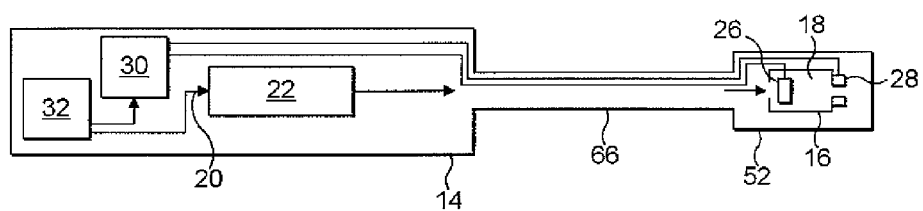
FIGS. 1 and 2 are schematic views of an embodiment of a device according to the present invention.
Figure 2:
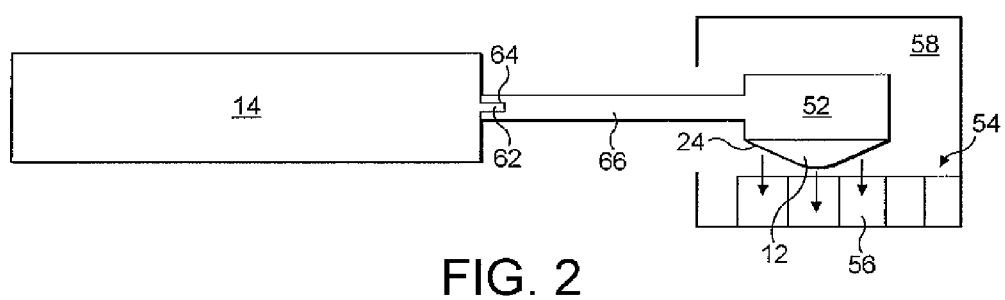

Referring to FIGS. 1 and 2, a device 10 is shown for generating a non-thermal gaseous plasma from a gas stream. Referring to FIG. 2, gas plume 12 containing ions and other chemically active species is emitted from the device. The device is configured to be hand-held and operated and therefore should be of a mass, size and shape enabling a typical user of the device to operate the device for treating a treatment region.

The device 10 comprises a housing 14 configured to be held by hand and in which the components of the device are housed. The housing also provides electrical insulation from high electrical potentials generated within the housing during use of the device.

A miniature plasma cell 16 defines a plasma forming region or volume 18 in which gas passing through a cell inlet 20 from a gas source 22 can be energised to form a non-thermal gaseous plasma and discharged through a cell outlet 24 for treatment of a treatment region by the resulting gaseous plume. The miniature plasma cell 16 may have a free gas of between 1 and 5 ml, or even less than 1 ml. The gas source is typically a sealed capsule of suitable plasma gas, typically comprising relatively pure helium, doped, if desired, with up to, say, 1000 ppm of active gas such as oxygen. The device may be provided with means such as a hollow piercing needle (not shown) for piercing the seal and releasing the gas there-from. The capsule may have a (water) capacity up to 100 ml, and typically about 20 ml. The plasma cell 16 is located in an applicator head 52. A plurality of electrodes 26, 28 are provided for receiving electrical power from a source of electrical power 30 for energising gas in the cell 16 to form a gaseous plasma. Although shown in a position within the cell 16, one or more of the electrodes 26, 28 may be positioned externally thereof.

The electrodes comprise at least one downstream electrode 28 and at least one upstream electrode 26 relative to the flow of gas through the cell. In FIG. 1, only a single downstream electrode is shown and a single upstream electrode. The downstream electrode is annular and located at the outlet 24 so that when plasma is formed it is conveyed towards the outlet. It will be seen therefore that the downstream electrode will be located closer in use to a treatment region of a patient or user, than the upstream electrode. The upstream electrode in one arrangement of FIG. 1 is an electrically conductive plate located at least partially or as shown fully within the cell. The plate is sized and located for generating generally uniform or homogeneous plasma in the volume 18 of the cell or at least in a greater part of the volume. The conductive part of the upstream electrode is in contact with gas in the cell and is not insulated by a dielectric or is at least substantially uninsulated.

The source of electrical power 30 may comprise a battery or a rechargeable battery, of relatively low voltage, say 12V, associated with appropriate electrical circuits of a kind known in the art, to produce a stepped-up AC or stepped-up pulsed DC voltage and in one arrangement is rated 1 kV at 2 mA. The voltage peaks may each endure for, say, 1 millisecond and may occur at intervals of, say, 5 to 10 milliseconds. When the source 30 is connected with electrode 26, an electrical potential is generated in the electrode 26 relative to the electrode 28. The electrical potential causes ionization of gas in the plasma cell which can be discharged through the cell outlet 24 in the form of plasma plume 12 for treating a treatment region of a user. The electrode 28 is maintained at low or zero electrical potential so that should a user accidentally touch the electrode, little or no current will pass avoiding any injury. Accordingly, even though electrode 26 is maintained in use at a high electrical potential, for example at least 1 kV (RMS), a user is protected by electrode 28 and also by the insulated housing 14.

Further, some gas molecules in the plasma cell can typically be ionised when the gas receives a given amount of energy to split apart the molecules or atoms into positively and negatively charged constituents. The gas may typically be based on helium. As electrode 26 is not insulated from the gas in the plasma cell by a dielectric, the electrical potential required to ignite the plasma is less than would be required with an insulated electrode. Accordingly, lower voltages may be used which conserves power allowing longer battery life.

A controller 32 is operably connected to both the source of electrical power 30 and to the source of gas 22 for both controlling activation of the electrodes and for controlled passage of gas into the plasma cell.

Figure 3:
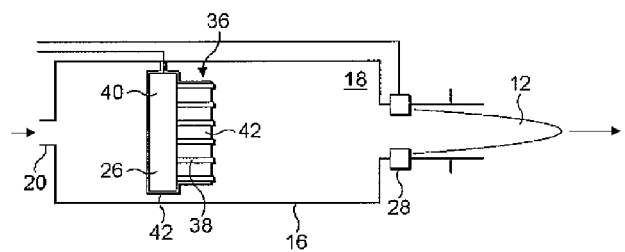
FIGS. 3 to 5 are schematic views of alternative plasma cells for use in the devices shown in FIGS. 1 and 2.

It has been found in use of the arrangement shown in FIG. 1 that when the electrodes are energised, even though the plate electrode 26 is sized to occupy a relatively large portion of the lateral dimension of the cell, that plasma may not consistently be ignited throughout the volume 18. Instead, a cascade effect may occur at a relatively small portion of the electrode 26 at which the majority of the electrical potential is discharged into the gas forming a path along which current is discharge from the electrode 26 to the electrode 28. When electrode 26 discharged in this way to electrode 28 the degree of ionisation of the total gas flow may become significantly reduced, and the resultant concentration of active species (neutral and ionised), as pertains to the activity of the plume 12, and therefore the efficiency of the system may therefore also be reduced. The arrangement shown in FIG. 3 provides an improved device for generating a generally uniform amount of plasma in the volume 18 of the plasma cell or at least in a greater volume of the cell compared to the FIG. 1 arrangement. This allows for greater contact with the un-ionised gas and therefore more efficient secondary reaction of the plasma, which may be important to the desired composition of the emergent plume 12.

Referring to FIG. 3, electrode 26 comprises an array of electrically conductive electrode portions 36 which are distributed relative to the plasma cell so that plasma is generated generally uniformly in the volume 18 of the cell or at least plasma is generated in a greater portion of the volume. The electrode portions 36 comprise respective electrical resistors 38 each being connected to an electrically conductive pad or portion which projects into the volume of the cell and a an electrical plate 40 for receiving electrical power from source 30. The electrical plate 40 and at least a portion of the resistors are insulated from the volume 18 of the cell by a dielectric 42, so that only the first ends of the electrode portions are exposed to gas in the cell.

In use of the FIG. 3 device, when electrode 26 is energised and gas is present in the plasma cell, any one of the plurality of electrode portions may initially be susceptible to a cascade effect as described above, since in the absence of a flow of current across the resistors the first ends that are exposed to the volume 18 have a potential generally the same as that of the source 30. That is, the potential does not drop across the resistor. When any one of the electrode portions ignites a plasma in the vicinity of the first end thereof, current flows and therefore there is drop of potential across the resistor. The resistance of the resistors is selected such that when plasma is ignited at one electrode portion, the potential at that electrode portion drops below the potential of the other resistors thereby increasing ignition of plasma at the other electrode portions. Accordingly, over a relatively short period of time, plasma generation occurs at all or at least most of the electrode portions so that plasma is generated in a relatively greater portion of the volume 18.

The amount of energy required to ignite a plasma is greater than the energy required to sustain a gaseous plasma. For example, the potential at the electrode 26 required to achieve initial ionisation of gas in the cell 16 may be a least 1 kV (RMS), but the potential at electrode 26 required to sustain the ignited gaseous plasma is less than that. The first ends of the electrode portions in FIG. 3 are initially maintained at a first potential selected to ignite a gaseous plasma. When a gaseous plasma is ignited at an electrode portion the potential drops across the resistor because of the flow of current. The resistance of the resistors is selected therefore so that the potential drops on ignition of a gaseous plasma to a second potential which is below the first potential and above, or approximately at, the potential required to sustain the plasma. Accordingly, the electrical power required to sustain plasma in the cell is reduced.

By way of example, the resistance of the resistors is selected to be 10 kΩ when the source of electrical power is rated at 1 kV (RMS) at 2 mA and the gas is helium or helium doped with for example water.

Figure 4:
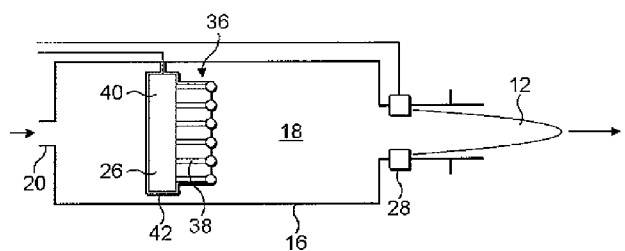

A further modification is shown in FIG. 4 in which the first ends 37 of the electrode portions 36 are generally rounded. In this example, electrically conductive generally spherical balls are provided at respective first ends of the electrode portions.

The rounded first ends are then insulated, together with the resistors and the electrical plate from the gas in the cell by dielectric 42, exposing only a portion of the rounded ends to gas in the cell. The rounded ends of the electrode portions spread potential which is otherwise concentrated at a tip of an electrode or at an angle thereof. The provision of rounded end therefore reduces the build up of potential and allows more predictable and uniform ignition of the plasma as well as reducing heating of the electrode portions.

Figure 5:
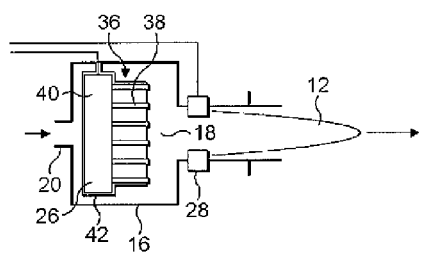

A further modification of the embodiment is shown in FIG. 5. In this modification, the spacing S between the electrode 26 and the electrode 28 is further miniaturised whilst still allowing sufficient flow of gas into the cell and between the electrodes for plasma generation. The spacing may in one arrangement be as little as 1 mm or even as little as 0.1 mm. In this regard, a reduction in the spacing between electrodes increases the efficiency of plasma generation for a given potential at the electrode 26.

Additionally, the volume 18 defined by the plasma cell is reduced providing a number of advantages. The provision of a miniaturised plasma cell allows the cell to be located in use close to or adjacent the treatment thereby reducing the distance that generated plasma must travel from the cell to the treatment region. This advantage may be useful if the half life of the active species is short. In this regard, the volume 18 of the cell is preferably less than 200 mm$^3$.

Referring again to FIGS. 1 and 2, the applicator head 52 configured for location adjacent a treatment region 54. The treatment region 54 in this example is the teeth 56 of a user in an oral cavity 58. Accordingly, as shown in FIG. 7, the applicator head 52 is configured for location in an oral cavity of a human or animal for treating the teeth or gingival of the human or animal.

The housing 14 has a connection portion 62 for connecting to a complementary demountably connecting portion 64 of the applicator head 52 so that when connected gas can be supplied to the cell 16 and the electrodes 26, 28 supplied with electrical power. The applicator head arrangement comprises neck portion 66 extending between the housing 60 and the applicator head 52 when connected.

The applicator head is sized to be received in an oral cavity and may be for example the size and shape of a typical tooth brush head. Accordingly, the cell 16 can be located in use as close as is practicable to the treatment region. Therefore, if the gas source supplies helium or doped helium, for example, giving beneficially active species having a short half life in the region of 1 millisecond, the concentration of active species in the plume emitted or ejected from the plasma cell 16 does not decay too much prior to beneficial contact with the treatment region. That is, the plume will still contain an acceptable concentration of ions and other active species, notwithstanding the fact that the active species may have quite short half lives.

The arrangement shown in FIGS. 1 and 2 allows the applicator head to be replaced with a new applicator head after continued use, without the requirement to replace the entire device. The proper functioning of the plasma cell arrangement may reduce after continued use, and therefore it is considered advisable for it be replaced regularly. In this way, the applicator head becomes a throw-away part, in a similar way to the applicator head of an electric tooth brush which also requires regular replacement.

A further advantage of a miniaturised plasma cell is that flushing, before each use of a device 10, the volume of the cell with gas from the gas source to clear the cell of contaminants prior to energising the electrodes to form a plasma is facilitated. In this regard, contaminants present in the cell on ignition of a plasma may form undesirable species which may either interfere with the action of desired species or produce an unwanted effect. An example of an undesirable species is ozone, which not only has a distinctive odour but can be safely tolerated by the user only in very low quantities.

A still further advantage of a miniaturised plasma cell is that a relatively small amount of gas may be energised to form a plasma per unit of time. Accordingly, in the example shown in FIG. 2, the oral cavity need not be flushed with the resulting plume most of which may not produce a therapeutic or beneficial effect. If small quantities of plume are provided to the treatment region a greater proportion of the plasma may achieve the required effect, whilst conserving gas and prolonging the life of the gas source between replacement or refilling.

What is claimed is:

1. A device for providing a flow of partially ionised non-thermal gaseous plasma for treatment of a treatment region, the device comprising:
    a housing containing a gas source and an electrical power source;
    an applicator head configured for location adjacent the treatment region and defining a plasma cell having a cell inlet and a cell outlet, the applicator head also having a plurality of electrodes;
    wherein the applicator head is detachable from the device and wherein gas from the gas source is delivered to the plasma cell through the cell inlet and is ionised by the electrodes using energy from the power source, and wherein the gaseous plasma is discharged to the treatment region through the cell outlet.

2. A device according to in claim 1, wherein the device is hand-held.

3. A device according to claim 1, wherein the device is formed as an attachment to an articulated arm that of a kind that is used to hold a dentist's drill.

4. A device according to claim 1, wherein the applicator head is configured and sized for insertion into an oral cavity of a human or animal for treating the teeth or gingival of the human or animal.

5. A device according to claim 4, wherein the applicator head is in the form of a brush.

6. A device according to claim 1, wherein the plasma cell has a free gas space of no more than 10 ml and wherein the plurality of electrodes comprises at least two electrodes spaced apart by no more than 10 mm.

7. A device according to claim 1, wherein the housing has a connection portion and the applicator head has a complementary connection portion that provides a means to connect the housing and the applicator head.

8. A device according to claim 1, wherein the electrical power source comprises a battery and at least one electrical circuit for converting the output of the battery into a pulsed DC or AC signal suitable for the generation of the non-thermal gaseous plasma.

9. A hand-held device for providing a flow of partially ionised non-thermal gaseous plasma for treatment of a treatment region, the device comprising:
    an applicator head containing a miniaturised plasma cell having a cell inlet for receiving gas from a gas source, defining a volume in which the gas received from the gas source is ionized to form the gaseous plasma, and having a cell outlet for discharging the gaseous plasma to the treatment region
    wherein the applicator head is detachable from the device.

10. A hand-held device according to claim 9, wherein the plasma cell has a free gas space of between 1 and 5 ml.

11. A hand-held device according to claim 9, wherein the plasma cell has a free gas space of less than 1 ml.

* * * * *